United States Patent [19]

Schmitt et al.

[11] Patent Number: 5,199,950
[45] Date of Patent: Apr. 6, 1993

[54] MEDICAL INSTRUMENT

[75] Inventors: Klaus Schmitt, Remshalden-Grunbach; Helmut Entenmann, Schorndorf-Schornbach, both of Fed. Rep. of Germany

[73] Assignee: Willy Rusch AG, Fed. Rep. of Germany

[21] Appl. No.: 748,667

[22] Filed: Aug. 22, 1991

[30] Foreign Application Priority Data

Dec. 7, 1990 [EP] European Pat. Off. ............ 90123498

[51] Int. Cl.$^5$ ............................................. A61M 37/00
[52] U.S. Cl. ...................... 604/95; 604/282; 128/772
[58] Field of Search ................ 604/95, 282; 128/4, 128/656–658, 772

[56] References Cited

U.S. PATENT DOCUMENTS

| 3,253,524 | 4/1966 | Ashizawa et al. | 128/4 |
|---|---|---|---|
| 3,470,876 | 10/1969 | Barchilon | 604/95 |
| 3,557,780 | 1/1971 | Sato | 128/4 |
| 3,605,725 | 9/1971 | Bentov . | |
| 3,773,034 | 11/1973 | Burns et al. | 604/95 |
| 3,892,228 | 7/1975 | Mitsui | 128/4 |
| 4,150,676 | 4/1979 | Jackson . | |
| 4,207,873 | 6/1980 | Kruy | 128/6 |
| 4,215,703 | 8/1980 | Willson . | |
| 4,294,233 | 10/1981 | Takahashi | 128/4 |
| 4,483,326 | 11/1984 | Yamaka et al. | 128/4 |
| 4,586,923 | 5/1986 | Gould . | |
| 4,633,882 | 1/1987 | Matsuo et al. | 128/4 |
| 4,659,195 | 4/1987 | D'Amelio et al. | 128/4 |
| 4,686,963 | 8/1987 | Cohen . | |
| 4,822,345 | 4/1989 | Danforth | 604/95 |
| 5,025,804 | 6/1991 | Kondo | 128/4 |
| 5,030,204 | 7/1991 | Badger et al. | 604/95 |

FOREIGN PATENT DOCUMENTS

| 0165718 | 5/1985 | European Pat. Off. . |
|---|---|---|
| 0259945 | 5/1987 | European Pat. Off. . |
| 0254885 | 6/1987 | European Pat. Off. . |
| 0254701 | 7/1987 | European Pat. Off. . |
| 1491697 | 12/1964 | Fed. Rep. of Germany . |
| 3214615 | 4/1982 | Fed. Rep. of Germany . |
| WO90/07355 | 1/1990 | World Int. Prop. O. . |

*Primary Examiner*—C. Fred Rosenbaum
*Assistant Examiner*—Mark Bockelman
*Attorney, Agent, or Firm*—Walter A. Hackler

[57] ABSTRACT

A medical instrument consists of a relatively rigid shaft (1) and a flexible tip (3) that is attached to one end of the shaft (1) as an extension thereof. Fastened to its outer end at points opposite each other are tension cables (5, 6), which are guided in a tubular sheath parallel to the tip (3) and to the shaft (1) to its other end, and at the other end of the shaft are joined to an adjusting wheel (8) that allows shortening of one and equal lengthening of the other of the two oppositely located tension cables (5, 6) in order to impart to the tip (3) a selectable curvature in the direction of the shortened tension cable. The invention has as its object a simplification of known instruments which simultaneously allows a reduction in dimensions. According to the invention the shaft (1) and the tip (3) consist of extruded plastic parts that are provided with conduits, located just under their surface, to accommodate the tension cables (5, 6) which are firmly joined to the tip (3), and the plastic parts are adhesively butt-bonded together at the transition (10) from shaft (1) to tip (3).

16 Claims, 3 Drawing Sheets

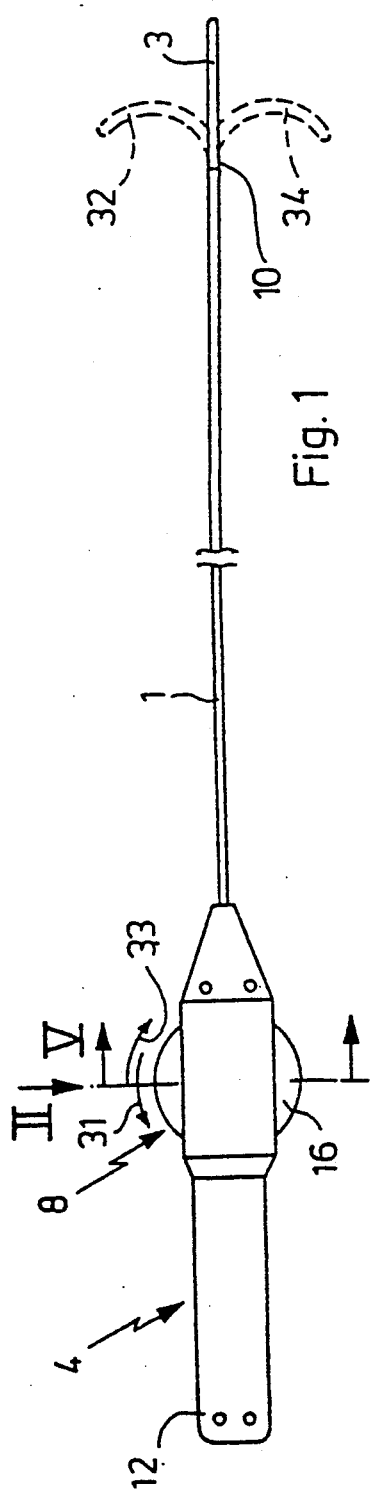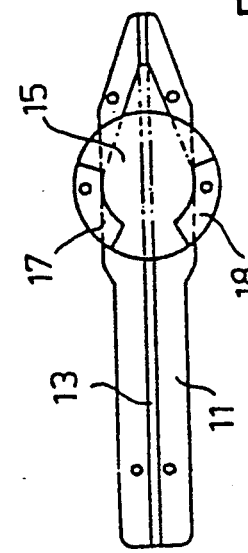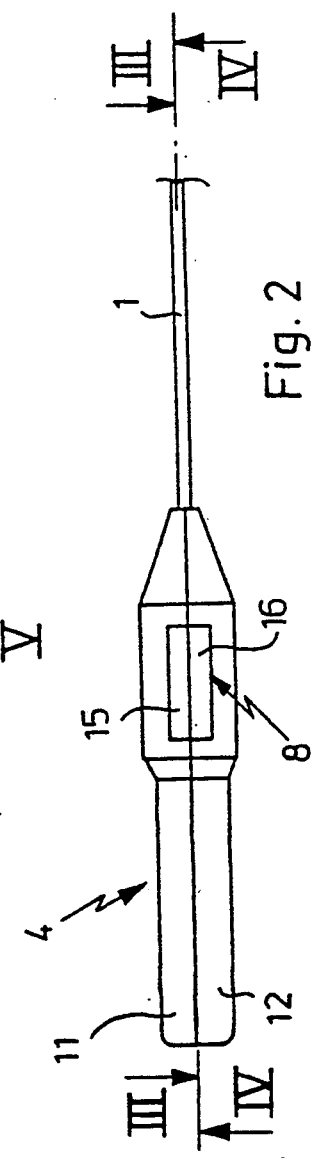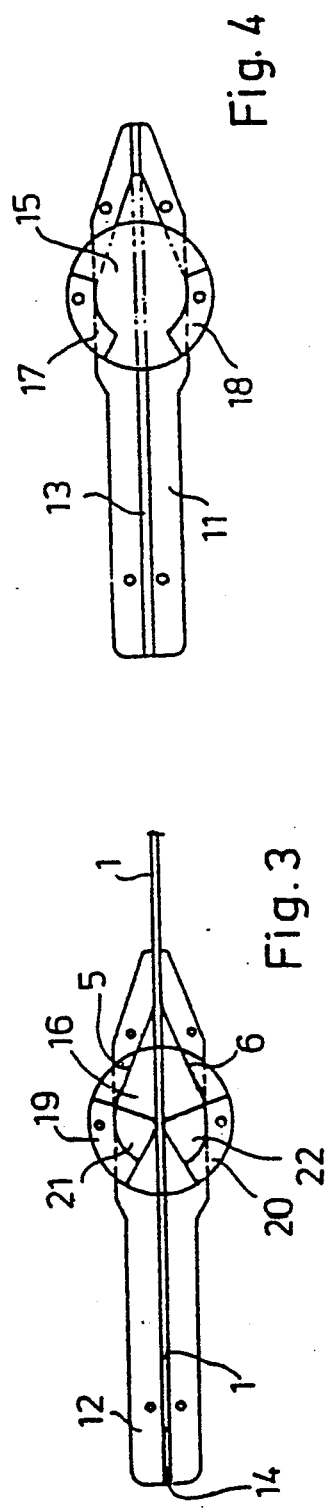

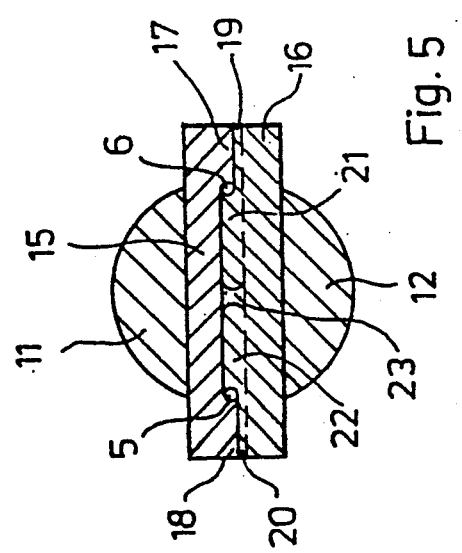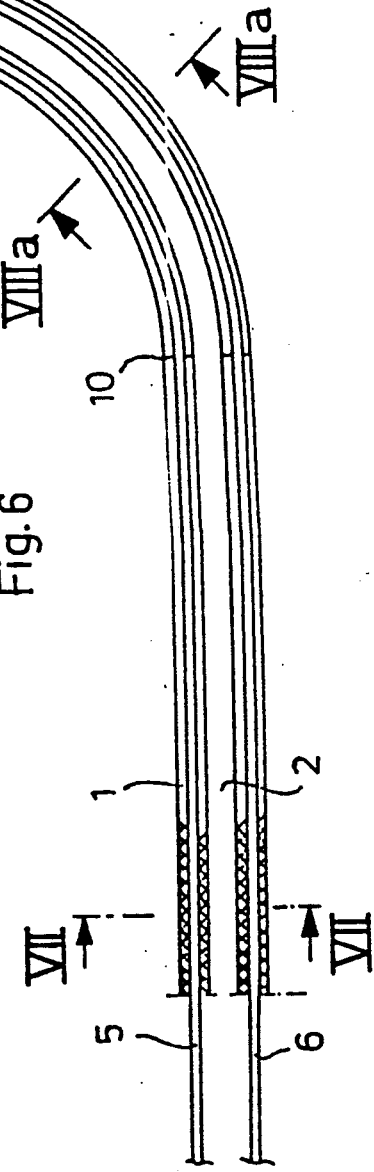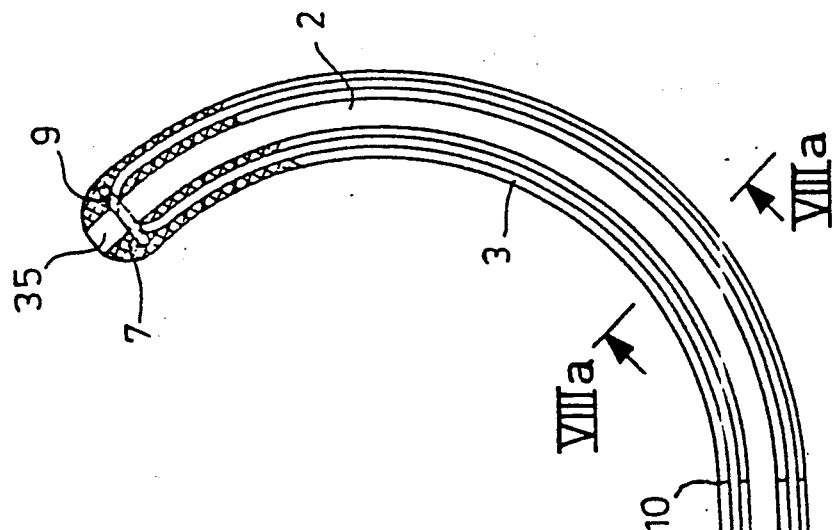

MEDICAL INSTRUMENT

BACKGROUND OF THE INVENTION

The invention relates to a medical instrument consisting of a relatively rigid shaft and a flexible tip, which is attached to one end of the shaft as an extension thereof and at whose outer end a tension cable can be fastened, that is guided essentially parallel to the tip and the shaft to its other end in a tubular sheath, and at the other end of the shaft is joined to an actuation element that allows a shortening of the tension cable so as to impart to the tip a selectable curvature in the direction of the shortened tension cable, and that the shaft and the tip consist of extruded plastic parts that are joined to one another at the transition from the shaft to the tip.

A catheter of this type has been disclosed by DE-OS 14 91 697.

Medical instruments of this kind are known, in the form of "controllable tip" endoscopes. The shaft consists of a relatively rigid metal or plastic tube, the interior of which, in larger-diameter endoscopes, is arranged as an instrument conduit, irrigation conduit, and the like; while thinner endoscopes, in the interest of particular miniaturization of their cross section, no longer have an actual lumen, but simply have a bundle of optical fibers passing through. The flexible tip of such endoscopes consists of a number of elements located one after the other and connected in an articulated manner to one another. Usually the cables of two Bowden wires are fastened, at two points opposite each other, to the element forming the outer end of the tip, and the sheaths of these cables are applied to the outer sides of the tip and the shaft and, in particular, are connected by means of a sheath surrounding the flexible tip and the shaft as well as the Bowden wires. Occasionally only one Bowden wire is used when it is possible to forego the ability to also re-extend the tip using Bowden wires. The curved tip can also be oriented by rotating the instrument about its longitudinal axis. In every case, the configuration of the known medical instruments which have a controllable tip at one end is relatively complex and requires a cross section of substantial size, which makes such an instrument unsuitable for many applications.

Operating methods in which relatively thin medical instruments are inserted into natural or artificial body conduits are becoming increasingly important. In such operations a controllable tip makes it possible to insert the instrument specifically into branching orifices or into those which, in the vicinity of body cavities, continue at an offset. Medical instruments with a precisely controllable tip are therefore suitable for many applications, and not only offer the operator new possibilities, but also guarantee gentler treatment of the patient.

SUMMARY OF THE INVENTION

The catheter disclosed by DE-OS 14 91 697 has a plastic shaft that can be welded to a tip which can be made of a plastic different from the shaft. Moreover the shaft, like the tip, is provided with an internal lumen that can accommodate a bending device. The rigidity of the catheter itself is achieved by various lattices that are incorporated into the plastic shaft material and into the tip. If the tip is to be swung out of its natural axis, the bending device, which consists of a guide tube and a flexible Bowden wire, must be pushed through the internal lumen to the vicinity of the tip. The Bowden wire is moved by actuating a lever at the end of the catheter away from the body, and the tip of the known catheter deflects. In addition to the complex structure of the bending device, it is disadvantageous that the central internal lumen of the bending device is occupied, and is not available for the insertion of additional instruments. Furthermore, both the outside diameter and the diameter of the internal lumen depend on the diameter of the bending device.

The object on which the invention is based is therefore that of simplifying a medical instrument of the aforesaid type and simultaneously developing it so that it can be manufactured even with extremely small diameters, so that a wide variety of medical instruments can be equipped with a precisely controllable flexible tip.

The object is achieved, according to the invention, by the fact that at least two conduits, each to accommodate one tension cable, which are firmly joined to the outer end, are provided just under the surface of the shaft and the tip.

Thus in the medical instrument according to the invention, a number of tubular sheaths for tension cables are integrated into the plastic parts forming the shaft and tip of the instrument, and are produced directly when these plastic parts are manufactured by extrusion. The parts made of materials of differing rigidity, namely the shaft and the tip, can be butt-joined in various ways, especially by simple adhesive bonding or welding. Not only is it surprising that it is possible to produce plastic extrusions with eccentric and extremely narrow conduits as sheaths for the tension cables, but it was also in no way immediately foreseeable that the plastic parts constituting the shaft and the tip could be butt-joined to one another in such a way that these conduits exactly align with each other and will not become blocked when the joint is made. Such a joint can, in addition, be made sufficiently firm to withstand all the stresses that occur during utilization of such an instrument, so that no danger exists of detachment of the tip and thus injury to the patient as a result of a tip that becomes detached and then cannot easily be removed.

Medical instruments configured according to the invention can be especially probes of any type, catheters, and the like. In these instruments as well, the shaft and the tip can have a central lumen that can serve as an aspiration and/or irrigation conduit, but also for the introduction of other instruments, especially light guides, ultrasonic transmitters for lithotripsy, and the like. Another example of a medical instrument that can be configured according to the invention is a probe for angioplasty, which has an expandable balloon in the tip region. These probes in particular have a very small diameter, and it is extremely advantageous that with the invention, these probes can also be provided with a precisely controllable tip allowing the probe to be inserted into branching vessels.

There are many possibilities available for fastening the tension cable to the outer end of the tip; in particular, they can be bonded in, pressed in, or embedded. The arrangement must, however, be such that there is no danger of the tension cable pulling out, which would make the tip impossible to control. A particularly reliable fastening method is achieved if, in a further embodiment of the invention, a ring to which the tension cables are fastened is located in the outer end of the tip. Another possibility arises if at least one pair of tension cables located opposite one another is fastened to the outer end of the tip. Specifically, the two tension cables of the pair can then consist of two sections of a continuous cable, the portion of which connecting the two tension cables at the end of the tip is embedded into the material constituting the tip. The use of a continuous tension cable also guarantees a practically nondetachable joint between the tension cable and the end of the flexible tip. If the shaft and the tip have a central lumen, the portion of the cable embedded into the end of the tip can form a loop surrounding the lumen. This keeps the lumen open, and at the same time the loop creates a very large-surface and thus very secure attachment of the cable to the end of the tip. The tip can also be provided with an opening that is connected to the central lumen.

The configuration of the medical instrument according to the invention also offers the possibility of connecting multiple tension cables with the actuation elements necessary for proper control of the tip in a particularly simple manner. For this purpose, in a preferred embodiment of the invention, the other end of the shaft is fastened in a handle, in the vicinity of which the conduit of the shaft guiding the tension cable is open to the outside and in which an adjusting wheel projecting out of the handle on both sides is rotatably mounted about a rotation axis perpendicular to the axis of the section of the shaft fastened in the handle, with the end of the tension cable fastened to the adjusting wheel.

If the instrument has at least one pair of tension cables located opposite one another, the ends of one pair of tension cables are advantageously fastened at two points that are symmetrical with respect to the direction of the shaft and the rotation axis of the adjusting wheel.

This arrangement makes it possible to hold the handle and at the same time to grasp the adjusting wheel projecting out of the handle with thumb and forefinger at two points opposite one another, and thus to turn it easily. With the shaft correspondingly fastened in the handle, it is thereby possible to bend the flexible tip of the instrument in the plane defined by the handwheel. Thus despite the very simple configuration of the medical instrument according to the invention, it is also very easy to handle. If necessary, two handwheels can also be fastened in the handle, so that two pairs of tension cables can be fastened around them, allowing the tip to be controlled in two planes perpendicular to one another.

In a preferred embodiment of the invention, the adjusting wheel is mounted at its periphery in an opening of the handle and has a central opening through which passes the section of the shaft fastened in the handle. This configuration of the adjusting wheel is particularly advantageous if the shaft of the instrument has a central lumen that is intended to be accessible from the end of the handle. The said embodiment makes it possible to pass the entire shaft through the handle, or to continue the lumen present in the shaft by means of a hole provided in the handle. At the same time, it offers the possibility of mounting the shaft in the handle over a relatively long length, resulting in a very secure attachment. The shaft can also be passed through the handle below the adjusting wheel, or the adjusting wheel is offset laterally so that it projects from the handle only on one side. A lever with a finger ring can also be applied to the adjusting wheel. This is useful and especially advantageous when an additional grip section is configured on the handle, so that the instrument can be held like a pistol and the tip can be easily and precisely deflected by a forward and backward motion of the finger by engaging the finger in the ring on the adjusting wheel.

In a further embodiment of the invention, the adjusting wheel can consist of two disc-shaped parts that have depressions and projections on their sides facing one another, which constitute the recesses for the shaft and guide surfaces for the end of the tension cable guided out of the shaft, respectively, and the end of the tension cable can be clamped between mutually contacting surface sections of the disc-shaped parts. This configuration of the adjustment wheel further improves the simplicity of the structure of the medical instrument, and moreover allows simple assembly.

It is evident that the instrument depicted is very simple in structure. The shaft and the tip can easily be produced by extrusion, and the individual parts can also be assembled in a simple fashion. The controllable tip of this catheter opens up many new possibilities, especially in lithotripsy, since the tip of the instrument, through the lumen of which a light guide or an ultrasonic transmitter can be inserted, can be precisely placed on a stone that is to be destroyed.

It goes without saying that the invention is not restricted to the exemplary embodiment illustrated, but rather that deviations therefrom are possible without leaving the scope of the invention. Especially, it is immediately recognizable that such an instrument can be provided with two pairs of tension wires which are located in two planes perpendicular to one another and are each connected to a separate adjusting wheel, so that the end of the flexible tip can be directed in any desired direction.

For pointing the tip of the instrument to a particular point, it is advantageous if this tip is opaque to X-rays, so that its location can be observed on the X-ray screen. For very sensitive adjustments, the use of three tension cable pairs might even be possible.

It is furthermore immediately evident that the invention can be realized in medical instruments that are specially configured for a number of different applications. These may be probes without a central lumen, but also instruments with several lumens that can serve as conduits for other instruments, for aspiration, for irrigation, for expanding a balloon attached to the tip of the instrument, and the like. For example, such an instrument can be used especially as a probe for angioplasty, in which the precisely controllable tip also allows the probe to be introduced into vessels branching off from a main vessel, which previously was not possible. Thus the invention opens up new and advantageous possibilities in many application fields for the investigation and treatment of a wide variety of conditions.

In a further configuration of the invention, in the region of the shaft inside the conduit the tension cables are encased in a sleeve. This has the advantage that tip control can be improved even further. The sleeves, made of metal or plastic, additionally stiffen the shaft over its entire length and keep it directionally stable when the tip of the catheter according to the invention is swung. This further limits possible bending of the shaft during swinging of the tip due to a change in the length of the tension cable. This feature makes the tip itself even more controllable.

In a further configuration of the invention, a side port that connects to the lumen of the catheter is provided on the handle. A liquid or gases or aerosols can be precisely introduced through this conduit into body cavities. If an additional instrument such as an optical system (for example made of glass fibers) or a gripping tool is introduced through the central lumen of the catheter according to the invention, an irrigation flow can be administered through the side port. This is especially advantageous when disintegrated stone fragments must be rinsed out from a body cavity (laser lithotripsy). In blood vessels and also in the gall bladder and in its system of cavities, and in the case of perforated ducts (salivary duct, bile duct), an irrigating flow of salt solution can ensure a clear view through an endoscope. Optical inspection of both vessels and vessel anastomoses is improved.

If, in a further embodiment of the invention, there are incorporated into the plastic material of the tip strips that are located with one narrow side facing one another, symmetrically and transverse to the axis of the shaft, with the narrow side facing the lumen, with the strips being in each case displaced 90 degrees with respect to the tension cables, both the shaft and the tip will then be further constrained and stabilized. The tip can then be swung in only one direction.

In a further configuration of the invention, a braid is incorporated into the plastic material of the shaft, giving the instrument according to the invention high torsional stability and allowing exact alignment of the tip even in the presence of rotary movements.

Further advantages are evident from the description and the attached drawing. In addition, the features of the invention mentioned above and those to be indicated later can each be used individually or in any combinations among them. The embodiments mentioned are not to be understood as a definitive enumeration, but rather are exemplary in nature.

BRIEF DESCRIPTION OF THE DRAWINGS

The invention is depicted in the drawing and will be explained in more detail with reference to exemplary embodiments which refer to the drawing, in which:

FIG. 1 is a side view of a medical instrument according to the invention;

FIG. 2 is a side view of the section of the instrument in FIG. 1 comprising the handle, in the direction of arrow II;

FIG. 3 is a section along line III—III through the arrangement according to FIG. 2;

FIG. 4 is a section along line IV—IV through the arrangement according to FIG. 2;

FIG. 5 is a section along line V—V through the instrument according to FIG. 1;

FIG. 6 is the tip of the instrument according to FIG. 1 at enlarged scale and in the curved state;

Figure 7:
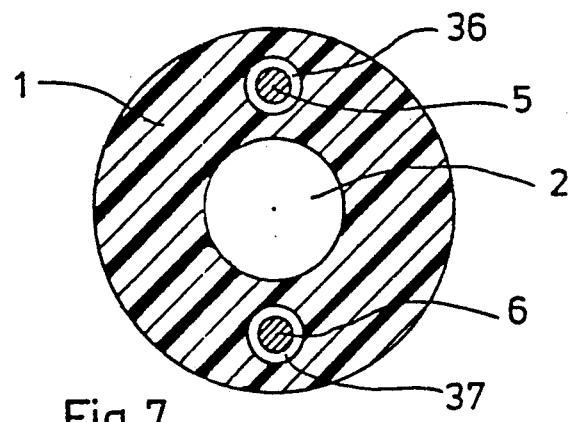
FIG. 7 is a section along line VII—VII in FIG. 6.

The individual Figures of the drawing in some cases show the subject of the invention in highly schematic form, and are not to be considered to scale. The subjects of the individual Figures are in some cases shown greatly enlarged so that their structure can be depicted better.

DETAILED DESCRIPTION

The medical instrument depicted in the drawing is a controllable instrument that comprises a shaft 1 in the form of a relatively rigid catheter tube with central lumen 2, to one end of which a flexible tip 3 is fastened, while its other end is fastened in a handle 4.

As FIG. 6 shows, the flexible tip 3 extends the shaft 1 and also continues the lumen 2 of the shaft 1 to the outer end 7 of the tip 3. Moreover, the shaft 1 and tip 3 have in their walls, at two locations lying opposite each other, conduits that form the guides for tension cables 5, 6. The tension cables 5, 6 are attached on the one hand to the outer end 7 of the tip 3, and on the other hand fastened, in a manner yet to be described, to an adjusting wheel 8 mounted rotatably in the handle 4, said attachment of the tension cables 5, 6 to the wheel 8 being symmetrical with respect to a longitudinal axis of the shaft 1. The two tension cables 5, 6 are sections of a common, continuous cable whose portion 9 joining the two tension cables 5, 6 forms a loop surrounding the lumen 2, which loop is embedded in the end 7 of the tip 3. This creates a very secure joint between the tension cables 5, 6 and the end 7 of the tip 3, while preventing the mounting of the tension cables 5, 6 from narrowing the lumen 2.

The relatively rigid shaft 1 and flexible tip 3 consist of extruded plastic parts that are adhesively butt-bonded to one another at the transition 10 between the shaft 1 and the tip 3. In the adhesive bonding, care was taken that not only the lumen 2 but also the conduits in the walls of the shaft 1 and the tip 3 accommodating the tension cables 5, 6 aligned exactly with one another and were not constricted or even clogged by adhesive.

The handle 4 consists of two shells 11, 12 which have a central groove 13 and 14 respectively to accommodate the shaft 1. When the two shells 11, 12 are combined to form the handle, for example are joined to one another with screws (not shown in more detail), the shaft 1 is solidly clamped in the bore formed by the grooves 13, 14. The adjusting wheel 8 is laid in corresponding recesses of the shells 11, 12 of the handle 4, and guided therein at its periphery. The adjusting wheel 8 consists of two disc-shaped parts 15, 16 which when the instrument is assembled are firmly joined to one another, for example by means of screws (not illustrated in more detail). The disc-shaped parts 15 and 16 contact one another along surface sections 17, 18 and 19, 20 located in the vicinity of their edges. In addition, the surfaces of the two disc-shaped parts 15, 16 facing one another opposite the surface sections 17, 18, which form sections of a circular ring, are recessed far enough so that the shaft 1 of the instrument can pass, with clearance, through the adjusting wheel 8 formed by the two parts. In the axial profile of the adjusting wheel 8, the shaft 1 does not run in a groove or bore, but touches the tips of sector-shaped sections 21, 22 only at single points. The tips are spaced apart, and the gap serves as a central recess 23 for the shaft 1 (FIG. 5). The sector-shaped sections 21, 22 applied onto the disc-shaped part 16, which project further above the surface sections 19, 20, contact the inner surface of the opposite part 15. These sector-shaped sections 21, 22 have outer rims lying on a circle, with which the ends of tension cables 5, 6 come into contact when they are gripped between the mutually contacting surfaces 17, 18 and 19, 20 of the disc-shaped parts 15, 16 of the adjusting wheel 8. The position of the tension cables 5, 6, which are guided out from corresponding lateral openings of the shaft 1, is illustrated in FIG. 3.

It is immediately evident that when the adjusting wheel 8 is rotated, tension is exerted on one of the tension cables 5, 6, while simultaneously the other tension cable 6 or 5 is relaxed, with the result that the flexible tip 3 at the end of the shaft 1 is bent to one side or the other, as illustrated with dashed lines in FIG. 1. The arrangement is configured so that the tip 3 bends in the same plane in which the adjusting wheel 8 is located, and also towards the side to which the adjusting wheel 8 is turned away from the tip 3. In other words, with the counterclockwise rotation indicated in FIG. 1 by the arrow 31, the tip 3 will be bent upwards as indicated by the dashed outline 32, while rotation in the opposite direction, namely in the direction of the arrow 33, will bring the tip 3 into the position 34 shown with dashed lines.

In FIG. 6, the tip 3 is provided with an opening 35. Fluids can be introduced through the opening 35 directly into a body cavity, or an additional instrument can be guided to this opening through the lumen 2.

FIG. 7 shows a section VII—VII of FIG. 6. The shaft 1 has, alongside the lumen 2, a conduit 36 and 37 in which the tension cables 5, 6 are guided. The shaft 1 itself is made of a flexible plastic.

Figure 8A:
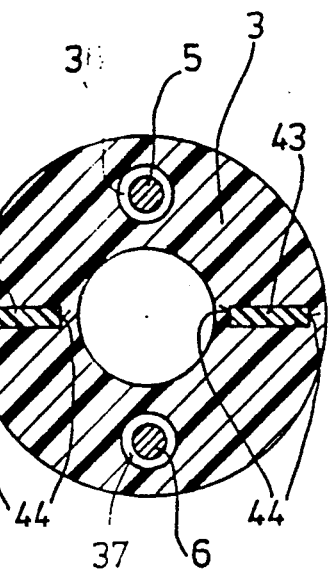
FIG. 8a is a section VIIIa—VIIIa of FIG. 6.
Figure 8:
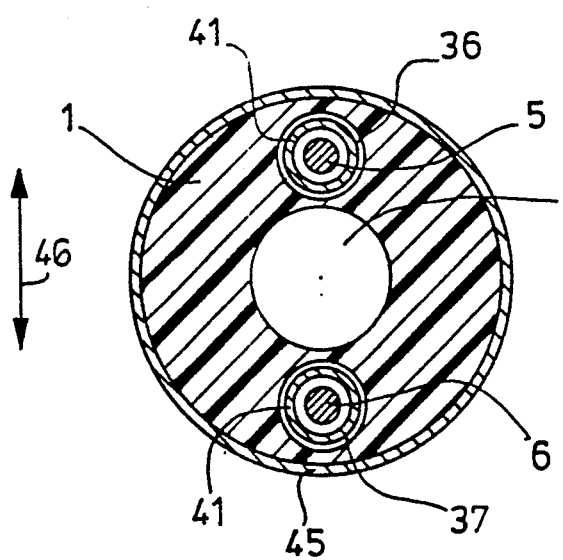
FIG. 8 is a further embodiment in section, corresponding to the section of FIG. 7.

FIG. 8 shows a further embodiment in section, indicating how the shaft 1 and the tip 3 can be configured. In FIG. 8 the shaft 1 is again provided with conduits 36, 37 which accommodate a sleeve 41 made of a bend-resistant material such as metal or hard plastic. The sleeves 41 end in the shaft 1 at the transition to the tip 3. The tension cable 5 or 6 is guided in the sleeve 41. The sleeve 41 stabilizes the shaft 1 against tension movements, and simultaneously increases the bending resistance of the shaft 1. The shaft 1 shown in the Figure is also encased in a braid 45 that additionally stiffens the shaft 1 and gives it high torsional stability.

FIG. 8a shows a cross section along section VIIIa—VIIIa of FIG. 6. Strips 43 are incorporated into the shaft section of the tip 3. These strips 43 can be metal or fabric strips, or also plastic strips. The strips 43 stabilize the tip 3 and counteract deflections of the tip 3 towards a narrow side 44 of the strips 43. In the embodiment shown, the tip 3 of the shaft 1 can move only in the arrow directions 46. The strips 43 prevent movement perpendicular to the arrow direction 46. The tension cables 5, 6 also run in conduits 37, 37 in the shaft section of the tip 3.

The minimum outside diameter of the shaft 1 and the tip 3 is approximately 1.5 mm, and the lumen 2 has a diameter of ca. 0.7 mm. The conduits 36, 37 each have a diameter of 0.25 to 0.3 mm. The strips 43 used are preferably 0.3 mm wide and 0.05 mm high. The tension cables 5, 6 are stainless steel strands with a diameter of approximately 0.15 mm.

Figure 9:
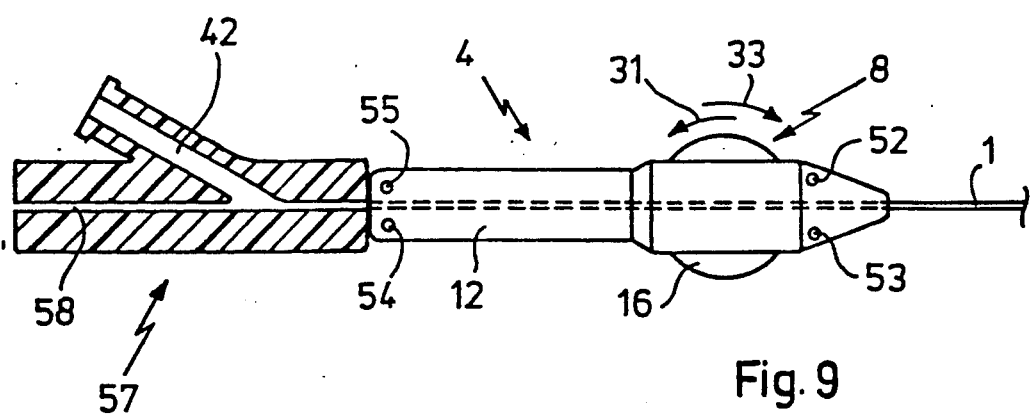
FIG. 9 is an instrument according to the invention with an add-on element with side port and a connection conduit coupled to the end of the handle.

FIG. 9 shows the shaft 1 with the handle 4, as also illustrated in FIG. 1. In addition to the medical instrument illustrated in FIG. 1, an add-on piece 57 is coupled to the end of the handle 4, and has a connecting conduit 58 that is connected to the lumen of the shaft 1. The shaft 1 is, as shown with dashed lines in the Figure, guided through the handle 4 and is separably joined to the connecting conduit 58. Rotary movements of the adjusting wheel 8 do not influence the position of the shaft 1 in the handle 4.

The shaft 1 is shown in FIG. 9 without a controllable tip. The tip can be swung by means of the two-part adjusting wheel 8, the disc-shaped part 16 of which is visible in the Figure, in the direction of the arrows 31, 33. The handle 4 is also configured in two parts and is held together by joining elements 52, 53, 54, 55, such as screws. The handle 4 is provided, at its end pointing away from the shaft 1, with a joining element by means of which the add-on piece 57 can be coupled to the handle 4. The add-on piece 57 also has a side port 42 that can be connected to conventional spray systems. A liquid or gases or aerosols can be delivered into the lumen of the shaft 1 via the side port 42. The side port 42 can have a valve or stopcock (not shown in the Figure) at its free end. In the vicinity of the open end of the connecting conduit 58, a septum can also be provided in the connecting conduit 58 itself and/or in the side port 42, to guarantee that a liquid delivered via the side port 42 can flow only into the lumen of the shaft 1 and through the handle 4. For example, a gripping tool or a fiber-optic system can be inserted through the connecting conduit 58 into the lumen of the shaft 1.

What is claimed is:

1. A medical instrument comprising:
    a relatively rigid shaft having a flexible tip attached to a distal end of the shaft, said shaft and tip each having a central lumen in fluid communication with one another;
    tension cables fastened to said flexible tip, said tension cables being guided essentially parallel to the tip and the shaft; and
    a handle fastened to the proximal end of the shaft with an adjusting wheel therein rotatably mounted about a rotation axis perpendicular to a longitudinal axis of the shaft, said tension cables being fastened to the adjusting wheel, the adjusting wheel having a central opening with the proximal end of said shaft inserted therein, said handle including means for rotating said adjusting wheel.

2. A medical instrument according to claim 1, wherein the tension cables are encased in a sleeve within said conduit means.

3. A medical instrument according to claim 1 wherein said shaft and tip comprise extruded plastic parts joined to one another and further comprising strips incorporated into the plastic material of the tip, said strips being disposed symmetrically and transverse to a tip axis with one narrow side of each strip facing one another, and also facing the central lumen, the strips being displaced 90° degrees with respect to the tension cables.

4. Medical instrument according to claim 1, wherein a braid is incorporated into the plastic material from which the shaft is formed.

5. A medical instrument according to claim 1, wherein the tension cables comprise two sections of a continuous cable having a distal portion connecting the two sections disposed at the distal end of the tip, said distal cable portion being embedded into the tip.

6. A medical instrument according to claim 5, wherein the portion of the tension cable embedded into the distal end of the tip forms a loop surrounding the lumen.

7. A medical instrument according to claim 1 further comprising a ring to which the tension cables are fastened, said ring being disposed in the distal end of the tip and conduit means for accommodating and guiding said tension cables, said conduit means being disposed just under a surface of the shaft and the tip.

8. A medical instrument according to claim 7 wherein the means for rotating the adjusting wheel comprises the adjusting wheel projecting out of the handle on both sides to permit manual rotation of the adjusting wheel and said handle is located in the vicinity of a position where the conduit means for guiding the tension cables is opened to the outside of the shaft.

9. A medical instrument according to claim 8 wherein proximal ends said tension cables are fastened at two points on the adjusting wheel, said two points being symmetrical with respect to the longitudinal axis of the shaft and the rotation axis of the adjusting wheel.

10. A medical instrument according to claim 8, wherein the adjusting wheel is mounted at its periphery in an opening of the handle.

11. A medical instrument according to claim 8, wherein the adjusting wheel comprises two disc-shaped parts each having depressions and projections on sides facing one another, said depressions and projections forming the central opening for the shaft and guide surfaces for ends of the tension cables guided out of the shaft, the proximal ends of the tension cables being clamped between mutually contacting surface sections of the disc-shaped parts.

12. A medical instrument according to claim 8 further comprising a side port communicating with the shaft lumen and connected to the handle.

13. A medical instrument comprising:
a relatively rigid shaft having a flexible tip attached to a distal end of the shaft, the shaft and the tip comprising of extruded plastic parts adjoined to one another at a transition from the shaft to the tip, said shaft and tip each having a lumen in fluid communication with one another;
tension cables fastened to the flexible tip, said tension cables being guided essentially parallel to the tip and the shaft to a proximal end of the shaft;
a handle fastened at the proximal end of the shaft with an adjusting wheel therein rotatably mounted about a rotation axis perpendicular to a longitudinal axis of the shaft, said tension cables being fastened to the adjusting wheel, the adjusting wheel having a central opening with the proximal end of said shaft inserted therein, said handle including means for rotating the adjusting wheel;
strips incorporated into the plastic material of the tip, said strips being disposed symmetrically and transverse to the tip longitudinal axis with one narrow side of each strip facing one another, and also facing the tip lumen.

14. A medical instrument according to claim 13, wherein said strips are displaced 90° with respect to the tension cables.

15. A medical instrument according to claim 13 wherein said means for rotating said adjusting wheel include the adjusting wheel projecting out of the handle on both sides thereof to permit manual rotation of the adjusting wheel.

16. A medical instrument according to claim 15 wherein the adjusting wheel comprises two disc-shaped parts, each having depressions and projections on sides facing one another, said depressions and projections forming the central opening and guide surfaces for ends of the tension cables, the ends of the tension cable being clasped between the disc-shaped parts.

* * * * *